United States Patent
Wood et al.

(10) Patent No.: US 10,839,520 B2
(45) Date of Patent: Nov. 17, 2020

(54) EYE TRACKING APPLICATIONS IN COMPUTER AIDED DIAGNOSIS AND IMAGE PROCESSING IN RADIOLOGY

(71) Applicant: National Institutes of Health, Rockville, MD (US)

(72) Inventors: Bradford J. Wood, Bethesda, MD (US); Haydar Celik, Bethesda, MD (US); Ulas Bagci, Oviedo, FL (US); Ismail Baris Turkbey, Rockville, MD (US)

(73) Assignee: The United States of America, as Represented by the Secretary, Department of Health & Human Services, Rockville, MD (US)

( * ) Notice: Subject to any disclaimer, the term of this patent is extended or adjusted under 35 U.S.C. 154(b) by 14 days.

(21) Appl. No.: 15/912,126

(22) Filed: Mar. 5, 2018

(65) Prior Publication Data
US 2018/0268552 A1    Sep. 20, 2018

Related U.S. Application Data

(60) Provisional application No. 62/466,516, filed on Mar. 3, 2017.

(51) Int. Cl.
| | |
|---|---|
| *G06T 7/194* | (2017.01) |
| *G16H 30/40* | (2018.01) |
| *G06T 7/00* | (2017.01) |
| *G06F 3/01* | (2006.01) |
| *A61B 6/00* | (2006.01) |

(Continued)

(52) U.S. Cl.
CPC .............. *G06T 7/194* (2017.01); *A61B 6/032* (2013.01); *A61B 6/5264* (2013.01); *A61B 6/582* (2013.01); *G06F 3/013* (2013.01); *G06K 9/00597* (2013.01); *G06K 9/4628* (2013.01); *G06T 7/0012* (2013.01); *G06T 7/11* (2017.01); *G16H 30/40* (2018.01); *A61B 6/463* (2013.01); *G06K 2209/05* (2013.01); *G06T 2207/10081* (2013.01); *G06T 2207/20101* (2013.01); *G06T 2207/20164* (2013.01); *G06T 2207/30064* (2013.01); *G06T 2207/30096* (2013.01); *G16H 50/20* (2018.01)

(58) Field of Classification Search
CPC ....... G06T 7/194; G06T 7/0012; G16H 30/40; G06F 3/013
See application file for complete search history.

(56) References Cited

U.S. PATENT DOCUMENTS

| | | | |
|---|---|---|---|
| 9,625,723 B2* | 4/2017 | Lou | .................... G02B 27/0172 |
| 9,936,195 B2* | 4/2018 | Horesh | .................. G06F 3/0304 |

(Continued)

*Primary Examiner* — Santiago Garcia
(74) *Attorney, Agent, or Firm* — Locke Lord LLP; Christopher J. Capelli; Judy R. Naamat (57) ABSTRACT

A system and method for using gaze information to extract visual attention information combined with computer derived local saliency information from medical images to (1) infer object and background cues from a region of interest indicated by the eye-tracking and (2) perform a medical image segmentation process. Moreover, an embodiment is configured to notify a medical professional of overlooked regions on medical images and/or train the medical professional to review regions that he/she often overlooks.

5 Claims, 4 Drawing Sheets
(3 of 4 Drawing Sheet(s) Filed in Color)

(51) Int. Cl.
  *A61B 6/03*    (2006.01)
  *G06T 7/11*    (2017.01)
  *G06K 9/00*    (2006.01)
  *G16H 50/20*   (2018.01)
  *G06K 9/46*    (2006.01)

(56) References Cited

U.S. PATENT DOCUMENTS

| | | | | |
|---|---|---|---|---|
| 2010/0220291 A1* | 9/2010 | Horning | | G02B 27/017 |
| | | | | 351/210 |
| 2013/0154918 A1* | 6/2013 | Vaught | | G06K 9/00617 |
| | | | | 345/156 |
| 2013/0187835 A1* | 7/2013 | Vaught | | G06F 3/013 |
| | | | | 345/8 |
| 2014/0049462 A1* | 2/2014 | Weinberger | | G06F 3/013 |
| | | | | 345/156 |
| 2014/0092014 A1* | 4/2014 | Srinivasan | | G06F 3/017 |
| | | | | 345/158 |
| 2014/0240217 A1* | 8/2014 | Lorenceau | | G02B 27/0093 |
| | | | | 345/156 |
| 2015/0003819 A1* | 1/2015 | Ackerman | | G02B 27/017 |
| | | | | 396/51 |
| 2015/0160461 A1* | 6/2015 | Starner | | G06F 3/013 |
| | | | | 345/156 |
| 2015/0212576 A1* | 7/2015 | Ambrus | | G06F 3/04842 |
| | | | | 345/156 |
| 2016/0048987 A1* | 2/2016 | Sevenster | | G06T 7/38 |
| | | | | 715/232 |
| 2016/0134863 A1* | 5/2016 | Horesh | | G06K 9/00604 |
| | | | | 348/78 |
| 2016/0309081 A1* | 10/2016 | Frahm | | G06K 9/00604 |
| 2017/0192502 A1* | 7/2017 | Dmitrieva | | A61B 5/168 |
| 2017/0263056 A1* | 9/2017 | Leppanen | | G06T 19/006 |
| 2017/0287112 A1* | 10/2017 | Stafford | | G06F 3/013 |
| 2017/0351326 A1* | 12/2017 | Aarts | | A61H 5/00 |
| 2017/0364722 A1* | 12/2017 | Todeschini | | G06K 7/10722 |
| 2018/0082482 A1* | 3/2018 | Motta | | G06F 1/163 |
| 2018/0158246 A1* | 6/2018 | Grau | | G02B 27/0093 |
| 2018/0314327 A1* | 11/2018 | Digirolamo | | G06K 9/3233 |

* cited by examiner

EYE TRACKING APPLICATIONS IN COMPUTER AIDED DIAGNOSIS AND IMAGE PROCESSING IN RADIOLOGY

CROSS-REFERENCE TO RELATED APPLICATIONS

This application claims priority to and the benefit of U.S. Provisional Application No. 62/466,516, filed Mar. 3, 2017, the entire contents of which are herein incorporated by reference in their entirety.

BACKGROUND

1. Field of Art

This disclosure relates, generally, to eye-tracking technology. More specifically, it relates to a system and method for tracking eye movement to increase the efficacy of visual diagnoses.

2. Background of Technology

Researchers have been trying to understand how radiologists can differentiate dangerous tumors from benign masses, and have begun using eye-tracking technology to aid in this research. It has been discovered that eye-tracking technology provides a novel method for increasing the efficacy of radiologists by permitting multimodal, hands-free interaction with context-sensitive displays.

Eye tracking is the process of measuring the point of gaze—where one is looking. An eye tracker is a device for measuring eye positions and eye movement. Eye trackers are used in research on the visual system, in psychology, in cognitive linguistics, in marketing, as an input device for human-computer interaction, and in product design.

There have been attempts to integrate both gaze information and attention information in radiology reading applications using eye-tracker systems. Studies have been conducted around 20 radiological images, such as mammograms and chest x-rays, but technical obstacles for volumetric data sets, such as lung CT images, have not been overcome. One of the biggest challenges for the application of eye tracking on 30 images, for example, is volumetric synchronization of eye-tracking data with the individual 2D slices. Another problem stems from interpreting the extensive and complicated data obtained from the eye-tracker and the high number of data sets.

Eye-tracking research can be categorized into two main branches. The first category uses eye-tracking information from a psychological viewpoint examining attentional behavior. The second category focuses on using eye-tracking information to interact with computers and perform a predetermined task. Current eye-tracking research focused on medical imaging mostly falls into the first category. Most studies in this category have been conducted to understand radiologists' visual search patterns, their differences, and expert and non-expert discriminations. Despite significant advances in human-computer interaction, the use of eye-tracking technology as an input to perform image analysis tasks in radiology remains untouched.

Such conventional methods and systems have generally been considered satisfactory for their intended purpose. However, there is still a need in the art for improved eye-tracking. This disclosure provides a solution for this need.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding embodiments of the disclosure, reference should be made to the following detailed description, taken in connection with the accompanying drawings, executed in color, in which.

DETAILED DESCRIPTION

In the following detailed description of certain embodiments, reference is made to the accompanying drawings, which form a part thereof, and within which are shown by way of illustration specific embodiments by which the disclosure may be practiced. It is to be understood that other embodiments may be utilized and structural changes may be made without departing from the scope of this disclosure.

This disclosure includes embodiments of a method and system that uses gaze information from an eye-tracker as an input for performing a real-time image segmentation task in radiology scans. Radiology scans include, but are not limited to, X-rays, magnetic resonance imaging, positron emission tomography, ultrasounds, and computed tomography.

The motivation for the use of eye-tracking in medical image segmentation task lies in the following facts. The segmentation process includes two relevant (and complementary) tasks: recognition and delineation. While delineation is the act of defining the spatial extent of an object boundary in the image, recognition (localization or detection) is the necessary step for determining roughly where the object is located. Automatic recognition is a difficult task; hence, manual or semi-automated methods are often devised for this purpose. Available automatic recognition methods usually employ an exhaustive search or optimization. This disclosure is able to use eye-tracking information as an effective recognition strategy for the medical image segmentation problems.

This disclosure employs an eye-tracker to gather gaze information, which is used as an input for performing real-time image segmentation of radiology scans. This disclosure applies a novel process that extrapolates gaze information to automatically create a medical image segmentation. The process is able to overcome the problems of current image segmentation technology, which require users to use a mouse for interactive segmentation of objects, or an automated method to define regions of interests. The latter, often called recognition, is more difficult as object detection is itself a big problem in image segmentation domain. Both options are costly in terms of efficiency.

Embodiments of this disclosure directly define the object of interest region using an attention based mechanism. In this regard, it is one of a kind approach. In addition, this disclosure combines attention regions (i.e., recognized regions) and processed images to define background and foreground cues, followed by a graph based algorithm to finalize boundary identification.

Currently, there is no segmentation algorithm working directly with eye tracking data. The field of Radiology, for example, will receive enormous benefits from this innovation as not only image analysis, but also real time eye tracking and object detection/segmentation with applications in surgery rooms, in interventional radiology applications, and in training radiology residents. The method and embodiments thereof presented herein is very efficient and fits the immediate needs of radiologists.

Figure 2A:
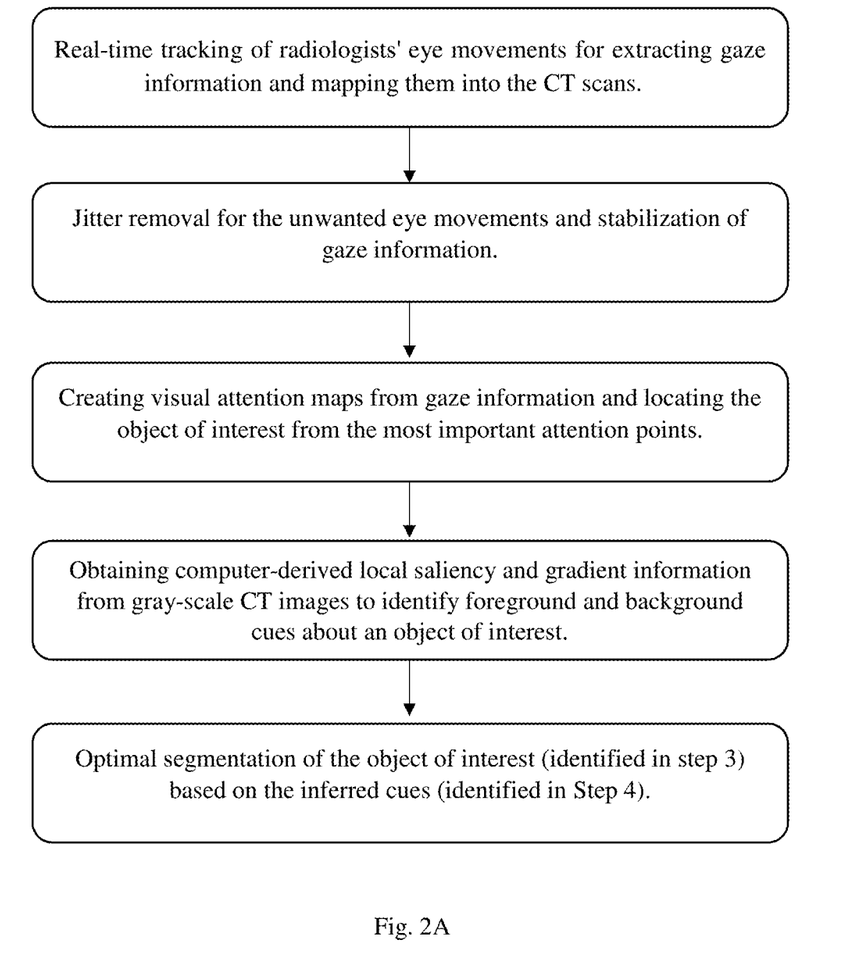
FIG. 2A is a flowchart depicting an embodiment of a method in accordance with this disclosure.
Figure 2B:
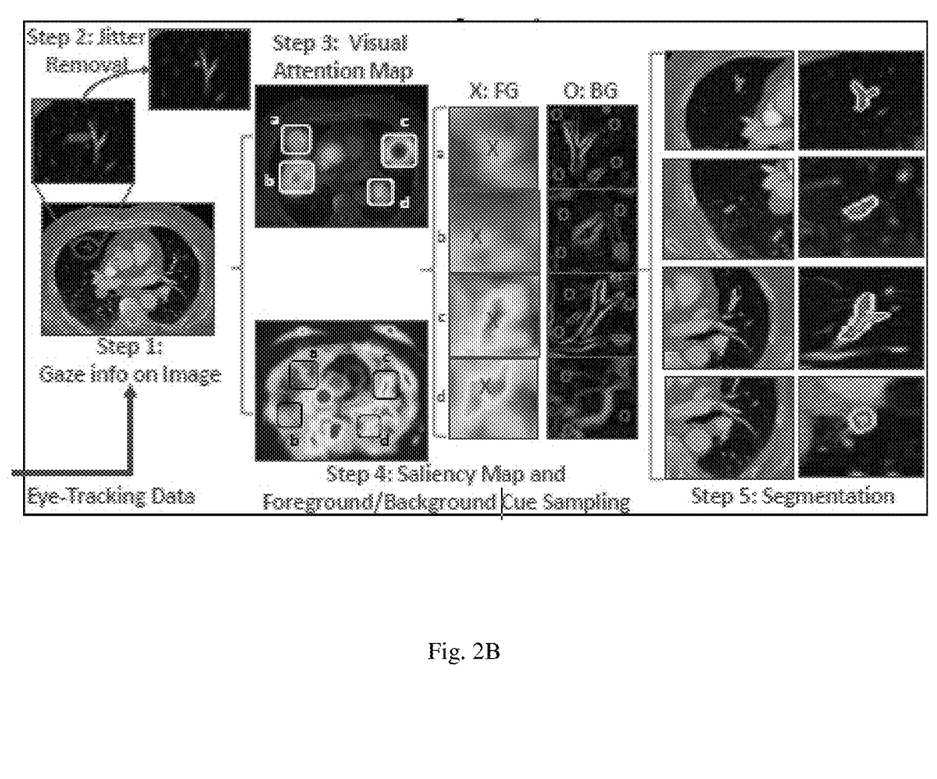
FIG. 2B is visual depiction of the five steps in the flowchart in FIG. 2A, shown in color.

An embodiment of the method of this disclosure can include the five steps depicted in FIGS. 2A-2B, which are summarized below:

Step 1. Real-time tracking of radiologists' eye movements for extracting gaze information and mapping them into the CT scans.

Step 2. Jitter Removal for the unwanted eye movements and stabilization of gaze information.

Step 3. Creating visual attention maps from gaze information and locating the object of interest from the most important attention points.

Step 4. Obtaining computer-derived local saliency and gradient information from gray-scale CT images to identify foreground and background cues about an object of interest.

Step 5. Optimal segmentation of the object of interest (identified in step 3) based on the inferred cues (identified in Step 4).

The above noted steps may be performed in any suitable order as appreciated by those having ordinary skill in the art in accordance with this disclosure. Also, any additional suitable steps or portions of a method can also be additionally performed, and/or any suitable portions of the above method may be eliminated or modified in any suitable manner.

Step 1: Eye-Tracking and Extracting Gaze Information

Eye-tracker technology having an eye-facing camera and scene-facing camera that attaches to eyewear, such as goggles or an empty frame in case the participating radiologist wears eyeglasses. The two cameras are adjustable to fit different users' settings. The eye-facing camera records the eye motion while the scene-facing camera (second camera, directed forward) records the monitor being observed by the radiologist. In an embodiment, the cameras record at a data rate of 60 Hz.

Figure 1:
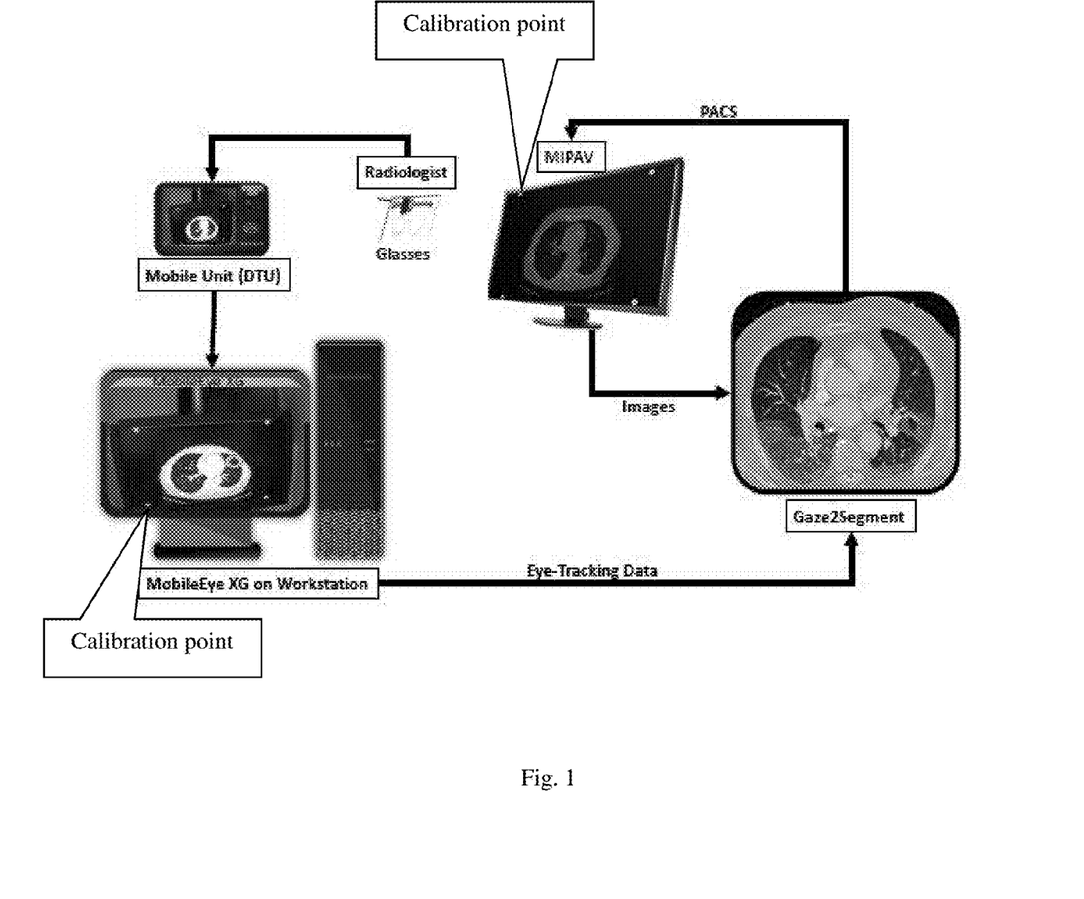
FIG. 1 is an embodiment of an embodiment of a system in accordance with this disclosure, shown in color.

The eye-facing camera monitors the pupil orientations and reflective angle using corneal reflection of, for example, three infrared dots on the eye from a reflective mirror. These dots are transparent to the visible spectrum and, therefore, do not obscure the radiologists' field of view. As depicted in FIG. 1, the data from these two cameras can be transferred to a workstation through a mobile display/transmit unit in real-time. The data may be transferred through one or more wires or wirelessly by any method known to a person of ordinary skill in the art.

Points of gaze are computed simultaneously on the scene image, which is preferably recorded at 60 frames per second with a range from 50-70 providing suitable performances. A calibration needs to be performed by the radiologist before every image reading experiment to match eye data and the scene video. The system outputs gaze coordinates with respect to the scene-facing camera's Field of View (FOV) and pupil diameter on, for example, a .csv file with a timestamp.

Once the calibrated gaze coordinates, scene video, and timestamp are created, gaze coordinates on the scene video ($g^v$) are converted to the gaze coordinates on the stimulus (i.e. scene or distal object on the scene) ($g^s$). This transformation is employed using the calibration information coming from the calibration points (white circles, placed on the screen FIG. 1). These points are automatically detectable by the eye-tracking technology for calibration. Further correction is always possible if the software incorrectly chooses a point other than these four.

Step 2: Jitter Removal and Gaze Stabilization

Eye-tracking data naturally contains jittery noises. While looking at a single object, users normally believe that they are looking at the object steadily, however, eyes have small jittery movements that create an unstable gaze location. The resulting noisy data could create instabilities in the system. In order to remove jitter noise, while preserving saccades, this disclosure uses a novel smoothing operator (J) as follows. Since gaze coordinates on the stimulus ($g^s$) include a set of points on the XY-coordinate system (i.e., planar), consecutive coordinate are assessed points by their Euclidean distance and the system eliminates those points that fall within a small neighborhood, which is defined as if $\|g^s(i) - g^s(i+1)\| \varepsilon$, then $g^s(i)$ is set to $g^s(i+1)$. As a result, all the pixels within the E-neighborhood are considered to be pertaining to the same attention regions.

In an embodiment, $\varepsilon$ is pre-defined as 7.5 mm. $\varepsilon$, however, can be defined based on different applications, data. and users. It is a simple constant defining how much the gaze data is smoothed. Based the experiments for all CT images with lung cancer detection, 7.5 mm was a good value when considering CT in-plane resolution a few mm pixel size. By consensus, gaze locations within 5-10 pixels were considered as jitter noise to be removed. Since pixel size is around 1 mm in-plane (xy-space), an average epsilon can be 7.5 mm (range: 5 mm to 10 mm). This physical value can change based on in-plane resolution, but number of pixels is considered as more reliable measure than the real physical distance.

Step 3: Visual Attention Maps

There are two major search patterns of radiologists for reading volumetric radiology scans: drilling and scanning. While drillers spend less time on a single area in one slice of an image and tend to scroll fast between slices (backward and forward), scanners spend more time on examining a single slice and then move to the next slice. Thus, it's a valid observation that radiologists spend more time on the regions that are more suspicious. Hence, the possibility of the presence of an abnormality in those areas is higher compared to the other areas. This fact is used to perform an image analysis task in suspicious areas of radiology scans.

Considering the above-mentioned information, as well as the theory of Von Helmholtz, which claims that eye movements reflect the will to inspect interesting objects in fine detail, although visual attention can still be consciously directed to peripheral objects. Time information (from the timestamp on the data) is used to create visual attention map as the regions to which radiologists divert their attention more than other points. Although the numerical value of the time spent on a specific area might be different between drillers and scanners, the time that is spent on potentially abnormal areas is relatively higher than other areas, regardless of search style, making time a reliable factor. For each gaze point on the stimulus $g^s(i)$, an attention value $a(i) \in [0,1]$ was created by mapping the corresponding timestamp $t(i)$ of the gaze coordinate in a piece-wise linear form as follows:

$$a(i) = \begin{cases} \dfrac{t(i) - \hat{t}}{t_{max} - \hat{t}}, & t(i) > \hat{t}, \\ 0, & \text{otherwise,} \end{cases} \quad (1)$$

where $t_{max}=\max_i t(i)$ and $\hat{t}$ can be set to 0 in order to assign an attention point for every gaze coordinate. However, for practical reasons, since many gaze coordinates may have very small timestamps associated with themselves (in milliseconds for instance), those gaze coordinates can be removed from the analysis by setting a larger $\hat{t}$.

Step 4: Local Saliency Computation for Foreground/Background Cue Sampling

In biological vision, humans tend to capture/focus on the most salient regions of an image. In computer vision, many algorithms have been developed to imitate this biological process by defining saliency with a different context. The most used definition of saliency is based on the distinctiveness of regions with respect to both their local and global surroundings. Although this definition is plausible for many computer vision tasks, it may not be suitable for defining salient regions in radiology scans where objects of interest may not be as distinctive as expected.

Therefore, this disclosure uses a context-aware saliency definition which can detect the image regions that represent the scene. The context-aware saliency detection method explains the visual attention with four feature-driven principles, three of which are implemented in this disclosure: local low-level considerations, global considerations, visual organization rules, and high-level factors.

For local low-level information, the image is divided into local patches ($p_i$) centered at pixel i, and for each pair of patches, their positional distance ($d_{position}$) and normalized intensity difference ($d_{intensity}$) are used to assess saliency of a pixel i: $d(p_i,p_j)=d_{intensity}/(1+\lambda d_{position})$, where $\lambda$ is a weight parameter. Pixel i is considered salient when it is highly similar to all other image patches, $d(p_i,p_j)$ is high $\forall j$.

For global considerations, a scale-space approach is utilized to suppress frequently occurring features, such as background, and maintain features that deviate from the norm. Saliency of any pixel in this configuration is defined as the average of its saliency in M scales $$R = \{r_1, r_2, \ldots, r_M\} \text{ as } \bar{S}_i = \left(\frac{1}{M}\right)\sum_{r\in R} S_i^r,$$

and $S_i^r$ is simply defined as $$S_i^r = 1-\exp\{-(1/K)\Sigma_{k=1}^K d(p_i^r,p_j^r)\} \text{ for } (r\in R) \quad (2)$$

This scale-based global definition combines K most similar patches for the saliency definition and indicates that there are more salient pixels i when $S_i^r$ is large.

For visual organization rules, saliency is defined based on the gestalt laws, suggesting areas that are close to the foci of attention should be explored significantly more than far-away regions. Hence, assuming $d_{foci}(i)$ is the Euclidean positional distance between pixel i and the closest focus-of-attention pixel, the saliency of the pixel is defined as $\hat{S}_i = \bar{S}_i(1-d_{foci}(i))$. A point is considered as a focus of attention if it's saliency is high (high saliency is larger than 0.5 in a saliency map running from 0 to 1). Since saliency map includes object of interest information, foreground information is extracted from this map (called foreground cues/seeds) by setting the most salient pixel in this region as a foreground cue.

For high-level factors such as recognized objects', position, size, appearance, and orientation can be applied as a post processing step to refine saliency definition. The method used for testing (discussed below) did not include this consideration, but an embodiment of this disclosure may include this consideration.

Since where information for objects of interest is inferred from visual attention map (Step 3), only what part of object of interest was explore from saliency definition. Once a saliency map is created, the analysis is restricted to the regions identified by corresponding visual attention maps (a(i)). Because the saliency map includes information on the objects of interest, foreground information is extracted from this map (called foreground cues/seeds) by simply setting the most salient pixel in this region as a foreground cue. This step helps relocate the attention gaze exactly to the center of the closest most salient object and allows a perfect seed selection.

In similar fashion, the background cues are defined for a given local region identified by the visual saliency map as follows. First, the gradient information $\nabla I$ is computed from, for example, a gray-scale CT image I. For a given visual attention map a(i) and saliency map S(i) at pixel i, a search is performed starting from $\nabla I(i)$ and moving in four perpendicular directions. The search concludes soon after passing through a high-intensity value on the gradient image because the object boundary locations show high gradient values due to abrupt intensity changes. The four pixels defined outside the object boundary are considered as background cues. This process is illustrated in FIG. 2 (steps 2 to 4).

Step 5: Image Segmentation

After identifying background and foreground seeds, any seed-based segmentation algorithm such as graph-cut, random walk (RW), and fuzzy connectivity, is used to determine the precise spatial extent of the object. This disclosure can utilize any suitable seed-based segmentation algorithm to implement fast, robust, and optimal image segmentation algorithm for a given set of seed points as appreciated by those having ordinary skill in the art (e.g., one or more conventional RW image segmentation algorithms).

Experimentation

An embodiment of this disclosure was tested using a stack of lung CT images pertaining to a patient diagnosed with lung cancer. The study focused on a realistic scan evaluation by a radiologist without inserting any environmental or psychological constraints. Unlike relatively simpler experiments with X-Rays, there are numerous slices to be evaluated in 3D CT images and radiologists may visit the same slice more than once, including changing the image views into axial, coronal and sagittal sections. Therefore, an image viewer plugin was developed for an open source medical image processing, analysis, and visualization software to record mouse manipulations, including scrolling, contrast change, and button clicks with the associated timestamp.

In-plane resolution of the images was 512×512 with each voxel size being 0.58×0.58×1.5 mm³. Imaging data and corresponding lesion labels and annotations were obtained from Lung Tissue Research Consortium (LTRC) (https://ltrcpublic.com/) with an institutional agreement. Blind to the diagnostic information of the chest CT scan, the participating radiologist (with more than 15 years of experience) read the scan once, and interpreted the results in real radiology settings. CT images with 10 different lung lesions as well as a few hundred slices without lesions were used for evaluation. Eye-tracking and extracted visual attention maps indicated that the participating radiologist detected all the lesions.

Figure 3:
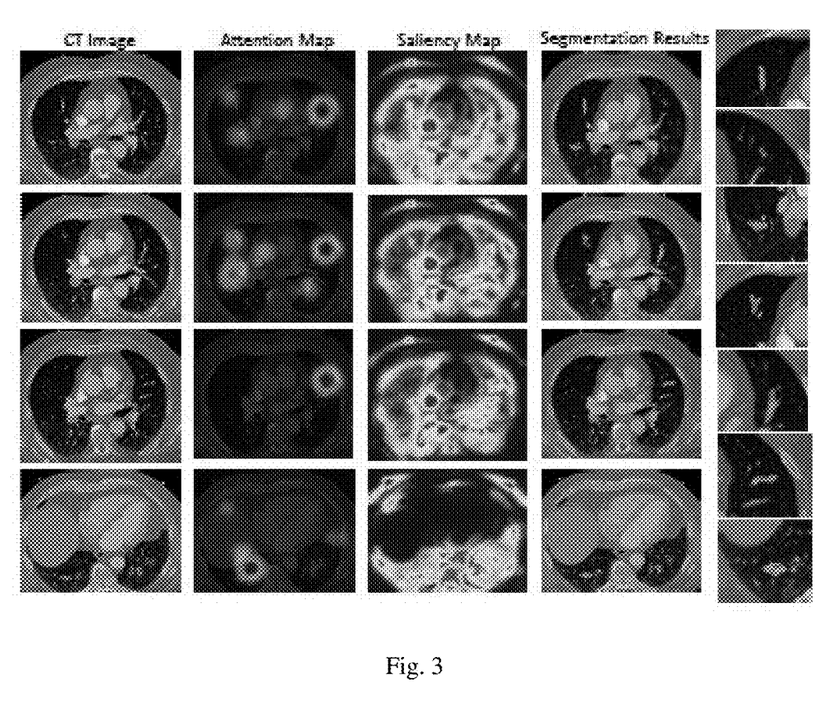
FIG. 3 is qualitative evaluation of medical image segmentation using this disclosure, shown in color.

FIG. 3 provides the experimental system's visual attention map, local saliency map, foreground/background seed samples, and resulting segmentation results at different anatomical locations. Data from the LTRC and manually obtained lesion boundary information from an expert interpreter was used as reference data for the experiment. The Dice Similarity coefficient (DSC) and Haussdorff Distance (HD) was used to evaluate the accuracy of the segmentation results over two ground truths. The average DSC was found to be 86% while average HD found to be 1.45 mm.

CONCLUSION OF EXPERIMENT

The results prove that an automated eye-tracking system integrated into the medical image segmentation process provides an improved method for segmenting medical images. Embodiments of the system successfully used radiologist's gaze information to extract visual attention information combined with computer derived local saliency information from the radiology images to (1) infer object and background cues from a region of interest indicated by the eye-tracking and (2) perform a medical image segmentation process. Furthermore, the experimentation proved that gaze information can be used effectively to address the recognition problem of image segmentation, causing a real-time quantification of radiology scans.

It should be noted that when different organs and imaging modalities are in consideration for a similar radiology reading experience, the methods presented herein should be adjusted based on the imaging characteristics and the saliency definition. Since saliency can be defined in multiple different ways, embodiments of a method presented herein may change parameters. For instance, CT imaging is an anatomical image modality and structures are observed with some hierarchy. If this method is used within PET images (Positron Emission Tomography), then saliency definition can be as simple as contrast information of the images. Then, the method's parameters can be adjusted easily. Also, for CT image with 5 mm resolution and 1 mm resolution can have different saliency parameters to capture details. Hence, one may change the parameter of saliency definition to make the method the most optimal for that resolution space. Changing the parameter is often straightforward because there is always a calibration step before performing eye-tracking experiments. That step could be used for such optimizations.

In certain embodiments, this disclosure can be used to identify sections of the medical image that has not been evaluated for diagnosis. Tracking the eye focal zone and the time dwelling at one location facilitates identification of tissue at risk for underdiagnoses. The system can then draw the radiologists attention to the region that was poorly evaluated or not yet evaluated.

These regions are determined based on the geography of what tissue has been looked at closely, versus what tissue has not been looked at closely. This could be refined by personalization of the algorithm for a specific radiologists given habit of reading and interpreting images, or more simply just defining a linear line of sight, and comparing high risk target tissue (i.e. segmented lung or peripheral lung, or high risk peripheral zone prostate) to create a distance map or linear distance from this line of sight created by tracking the eye motion. Any part of an image that has not been near the line of sight would then be identified as comparably far from this line (identified by a distance map algorithm), and tagged for further evaluation as tissue at risk for under-diagnosis.

In certain embodiments, personalized models of image interpretation methods can be built and one or more models can be trained to learn a MD's weak spot or areas where he or she may differ from other radiologists who interpret similar medical images. In this fashion, embodiments of an algorithm (e.g., embodied in a computer program module (e.g., having any suitable hardware and/or software)) can analyze an individual (personalized learning plan) or can compare that individual to a body of data from a body of readers to identify areas for weakness or areas where tumors might be missed or not seen during screening.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

The advantages set forth above, and those made apparent from the foregoing description, are efficiently attained. Since certain changes may be made in the above construction without departing from the scope of this disclosure, it is intended that all matters contained in the foregoing description or shown in the accompanying drawings shall be interpreted as illustrative and not in a limiting sense.

It is also to be understood that the following claims are intended to cover all of the generic and specific features of embodiments herein described, and all statements of the scope of this disclosure that, as a matter of language, might be said to fall therebetween.

Any suitable combination(s) of any disclosed embodiments and/or any suitable portion(s) thereof is contemplated therein as appreciated by those having ordinary skill in the art.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A method of automatically segmenting at least one medical image using eye-tracking technology, comprising:
   initiating eye-tracking software on an eye-tracker system having an eye-facing camera and a scene-facing camera;
   monitoring eye-movement data captured in the eye-facing camera and recording gaze information;
   transferring gaze information to a workstation;
   creating a two-dimensional visual attention map from the gaze information for respective regions of the at least one medical image for which the gaze information satisfied an attention criteria, each of the respective regions corresponding to a portion of one or more of the at least one medical images;
   obtaining local saliency and gradient information from the at least one medical image for each of the individual regions;
   identifying, individually for each of the regions, foreground and background cues as a function of at least one of the local saliency and gradient information obtained for the region; and
   automatically segmenting, individually for each of the regions, an object of interest associated with the region based on the background cues.

2. The method of claim 1, wherein the step of monitoring eye movement includes monitoring a user's pupil orientations and reflective angle using corneal reflections of infrared dots on a user's eye from a reflective mirror.

3. The method of claim 1, wherein the gaze information includes time stamps and gaze coordinates.

4. The method of claim 1, wherein the gaze information includes pupil diameter.

5. A system for automatically segmenting at least one medical image using eye-tracking technology, comprising:
   an eye-tracker system having an eye-facing camera and a scene-facing camera;
   eye-tracking software configured to monitor eye-movement data captured in the eye-facing camera and to record gaze information;
   a workstation in communication with the eye-tracker system to receive gaze information from the eye-tracker system, the work station further including software configured the execute the steps of:
   creating a two-dimensional visual attention map from the gaze information for respective regions of the at least one medical image for which the gaze information satisfied an attention criteria, each of the respective regions corresponding to a portion of one or more of the at least one medical images;
   obtaining local saliency and gradient information from the at least one medical image for each of the individual regions to identify individually for each of the regions, foreground and background cues as a function of at least one of the local saliency and gradient information obtained for the region; and automatically segmenting, individually for each of the regions, an object of interest associated with the region based on the background cues.

\* \* \* \* \*

UNITED STATES PATENT AND TRADEMARK OFFICE
CERTIFICATE OF CORRECTION

PATENT NO. : 10,839,520 B2
APPLICATION NO. : 15/912126
DATED : November 17, 2020
INVENTOR(S) : Bradford J. Wood et al.

Page 1 of 1

It is certified that error appears in the above-identified patent and that said Letters Patent is hereby corrected as shown below:

On the Title Page

Item (73), Assignee, insert:
--University of Central Florida Research Foundation, Inc., Orlando, Florida--

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*